(12) United States Patent
Jianhui

(10) Patent No.: US 7,709,653 B2
(45) Date of Patent: May 4, 2010

(54) ASYMMETRIC CYANINE COMPOUNDS, THEIR PREPARATION METHODS AND THEIR USES

(75) Inventor: Shao Jianhui, Shenzhen (CN)

(73) Assignee: Shenzhen Mindray Bio-Medical Electronics Co. Ltd., Shenzhen (CN)

( * ) Notice: Subject to any disclaimer, the term of this patent is extended or adjusted under 35 U.S.C. 154(b) by 0 days.

(21) Appl. No.: 12/482,335

(22) Filed: Jun. 10, 2009

(65) Prior Publication Data

US 2009/0305285 A1 Dec. 10, 2009

(30) Foreign Application Priority Data

Jun. 10, 2008 (CN) .................. 2008 1 0067815

(51) Int. Cl.
*C07D 293/10* (2006.01)
*G01N 33/00* (2006.01)
*C12Q 1/68* (2006.01)

(52) U.S. Cl. .................. 548/120; 548/121; 436/91; 436/800; 435/6; 435/7.1; 435/7.2

(58) Field of Classification Search .................. 548/120, 548/121; 436/91, 800; 435/6, 7.1, 7.2
See application file for complete search history.

(56) References Cited

U.S. PATENT DOCUMENTS

| | | | |
|---|---|---|---|
| 3,883,274 A | 5/1975 | Lawrence | |
| 4,122,348 A | 10/1978 | Abraham | |
| 4,146,604 A | 3/1979 | Marcos | |
| 4,286,963 A | 9/1981 | Stephen et al. | |
| 4,325,706 A | 4/1982 | Russell et al. | |
| 4,332,785 A | 6/1982 | Robert et al. | |
| 4,336,029 A | 6/1982 | Peter | |

(Continued)

FOREIGN PATENT DOCUMENTS

CN 1101980 4/1995

(Continued)

OTHER PUBLICATIONS

U.S. Appl. No. 12/334,274, filed Dec. 12, 2008, Jianhui Shao.

(Continued)

*Primary Examiner*—Jezia Riley
(74) *Attorney, Agent, or Firm*—Kory D. Christensen; Matthew S. Bethards; Stoel Rives LLP

(57) ABSTRACT

Asymmetric cyanine compounds represented by general formula I are provided, wherein X, n, $R_1$, $R_2$, $R_3$, $R_4$ and $Y^-$ are as defined in the specification. They have a maximum absorption peak at about 640 nm which may not change with ambient temperature. When the compounds bind a nucleic acid to form a dye/nucleic acid complex, the fluorescence intensity of the complexes will increased rapidly, so that they can be used as a staining agent for nucleic acids in flow cytometers. Their spectra are in the near-infrared region, which can effectively reduce the interference from background fluorescence and improve the accuracy of detection. Moreover, the compounds provided can also be used as a staining agent for blood reticulocytes.

Formula I

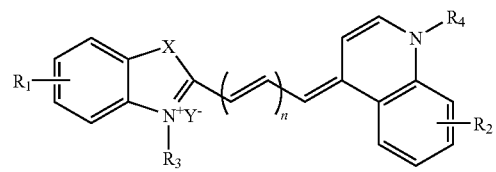

15 Claims, 13 Drawing Sheets

U.S. PATENT DOCUMENTS

| | | |
|---|---|---|
| 4,414,325 A | 11/1983 | Masuda et al. |
| 4,447,547 A | 5/1984 | Robert et al. |
| 4,485,175 A | 11/1984 | Stephen et al. |
| 4,528,274 A | 7/1985 | James et al. |
| 4,529,705 A | 7/1985 | Fred |
| 4,544,546 A | 10/1985 | Wang et al. |
| 4,571,388 A | 2/1986 | James et al. |
| 4,596,035 A | 6/1986 | Russell et al. |
| 4,617,275 A | 10/1986 | Matsuda et al. |
| 4,637,986 A | 1/1987 | Michael et al. |
| 4,707,451 A | 11/1987 | Sage et al. |
| 4,745,071 A | 5/1988 | James et al. |
| 4,751,179 A | 6/1988 | Stephen et al. |
| 4,822,745 A | 4/1989 | Edward et al. |
| 4,882,284 A | 11/1989 | Stefan et al. |
| 4,883,867 A | 11/1989 | Linda et al. |
| 4,933,293 A | 6/1990 | Kuroda et al. |
| 4,957,870 A | 9/1990 | Lee et al. |
| 4,971,917 A | 11/1990 | Kuroda |
| 4,978,624 A | 12/1990 | John et al. |
| 4,981,803 A | 1/1991 | Kuroda |
| 4,985,174 A | 1/1991 | Kuroda et al. |
| 5,039,613 A | 8/1991 | Matsuda et al. |
| 5,075,556 A | 12/1991 | Sophie et al. |
| 5,116,539 A | 5/1992 | Hamaguchi et al. |
| 5,155,044 A | 10/1992 | Stephen et al. |
| 5,175,109 A | 12/1992 | Sakata et al. |
| 5,179,026 A | 1/1993 | Matsuda et al. |
| 5,180,677 A | 1/1993 | Ludmilla et al. |
| 5,188,935 A | 2/1993 | Robert et al. |
| 5,227,304 A | 7/1993 | Wong |
| 5,232,857 A | 8/1993 | Lefevre et al. |
| 5,242,832 A | 9/1993 | Sakata |
| 5,250,437 A | 10/1993 | Toda et al. |
| 5,264,369 A | 11/1993 | Sakata et al. |
| 5,284,771 A | 2/1994 | Sophie et al. |
| 5,316,725 A | 5/1994 | Carver et al. |
| 5,316,951 A | 5/1994 | Carver et al. |
| 5,321,130 A | 6/1994 | Yue et al. |
| 5,350,695 A | 9/1994 | Gregory et al. |
| 5,360,739 A | 11/1994 | Sophie et al. |
| 5,389,549 A | 2/1995 | Hamaguchi et al. |
| 5,411,891 A | 5/1995 | Sophie et al. |
| 5,413,938 A | 5/1995 | Tsujino et al. |
| 5,438,003 A | 8/1995 | Gregory et al. |
| 5,486,477 A | 1/1996 | Carver et al. |
| 5,492,833 A | 2/1996 | Carlos et al. |
| 5,496,734 A | 3/1996 | Sakata et al. |
| 5,510,267 A | 4/1996 | Paul |
| 5,516,695 A | 5/1996 | Young et al. |
| 5,518,928 A | 5/1996 | John et al. |
| 5,538,893 A | 7/1996 | Sakata et al. |
| 5,559,037 A | 9/1996 | Young et al. |
| 5,563,070 A | 10/1996 | Yamamoto et al. |
| 5,616,501 A | 4/1997 | Carlos et al. |
| 5,618,733 A | 4/1997 | Sakata et al. |
| 5,633,167 A | 5/1997 | Sophie et al. |
| 5,639,630 A | 6/1997 | Michael et al. |
| 5,639,666 A | 6/1997 | Mark et al. |
| 5,656,449 A | 8/1997 | Stephen |
| 5,677,183 A | 10/1997 | Takarada et al. |
| 5,686,308 A | 11/1997 | Li et al. |
| 5,691,204 A | 11/1997 | Young et al. |
| 5,731,206 A | 3/1998 | Stephen et al. |
| 5,733,784 A | 3/1998 | Robert et al. |
| 5,747,343 A | 5/1998 | Tsuchiya et al. |
| 5,763,280 A | 6/1998 | Li et al. |
| 5,773,299 A | 6/1998 | Kim et al. |
| 5,786,224 A | 7/1998 | Li et al. |
| 5,817,518 A | 10/1998 | Li et al. |
| 5,821,127 A | 10/1998 | Akai et al. |
| 5,821,128 A | 10/1998 | Rene |
| 5,840,515 A | 11/1998 | Rene |
| 5,843,608 A | 12/1998 | Li et al. |
| 5,858,667 A | 1/1999 | Stephen et al. |
| 5,874,311 A | 2/1999 | Li et al. |
| 5,879,900 A | 3/1999 | Young et al. |
| 5,882,934 A | 3/1999 | Li et al. |
| 5,891,731 A | 4/1999 | Akai et al. |
| 5,928,949 A | 7/1999 | Sakata et al. |
| 5,958,776 A | 9/1999 | Sakata et al. |
| 5,968,832 A | 10/1999 | Uchihashi et al. |
| 5,994,089 A | 11/1999 | Olavi et al. |
| 5,994,138 A | 11/1999 | Veriac |
| 6,004,816 A | 12/1999 | Mizukami et al. |
| 6,060,322 A | 5/2000 | Allan et al. |
| 6,100,038 A | 8/2000 | Stephen et al. |
| 6,114,130 A | 9/2000 | Sylvie et al. |
| 6,114,173 A | 9/2000 | David et al. |
| 6,197,593 B1 | 3/2001 | Deka et al. |
| 6,245,499 B1 | 6/2001 | Suzuki et al. |
| 6,271,035 B1 | 8/2001 | Deka et al. |
| 6,287,791 B1 | 9/2001 | Leon et al. |
| 6,350,613 B1 | 2/2002 | Stephen et al. |
| 6,368,864 B1 | 4/2002 | Chiranjit et al. |
| 6,495,692 B1 | 12/2002 | Wang et al. |
| 6,524,858 B1 | 2/2003 | David et al. |
| 6,551,831 B2 | 4/2003 | Ravinder et al. |
| RE38,131 E | 6/2003 | Uchihashi et al. |
| 6,630,990 B2 | 10/2003 | Ronny et al. |
| 6,632,676 B1 | 10/2003 | Harold et al. |
| 6,664,110 B1 | 12/2003 | Tsuji et al. |
| 6,794,152 B2 | 9/2004 | Wayne et al. |
| 6,869,798 B2 | 3/2005 | Harold et al. |
| 6,900,023 B1 | 5/2005 | Berend et el. |
| 6,955,872 B2 | 10/2005 | John et al. |
| 6,977,156 B2 | 12/2005 | Wayne et al. |
| 7,083,982 B2 | 8/2006 | Wang et al. |
| 7,235,404 B2 | 6/2007 | Russell et al. |
| 7,247,484 B2 | 7/2007 | Wu et al. |
| 7,300,797 B2 | 11/2007 | Andre et al. |
| 7,405,082 B2 | 7/2008 | Mizukami et al. |
| 7,449,337 B2 | 11/2008 | Deka et al. |
| 7,465,584 B2 | 12/2008 | Matsumoto et al. |
| 2002/0182623 A1 | 12/2002 | Didier et al. |
| 2003/0145394 A1 | 8/2003 | Wang et al. |
| 2004/0241769 A1 | 12/2004 | Harold et al. |
| 2005/0202400 A1 | 9/2005 | Tsuji et al. |
| 2005/0272026 A1 | 12/2005 | Oguni |
| 2006/0177347 A1 | 8/2006 | Larsen et al. |
| 2007/0111276 A1 | 5/2007 | Didier et al. |
| 2007/0178597 A1 | 8/2007 | Tsuji et al. |
| 2008/0026475 A1 | 1/2008 | Andre et al. |
| 2008/0131898 A1 | 6/2008 | Tsuji et al. |
| 2008/0311898 A1 | 6/2008 | Tsuji et al. |
| 2008/0176274 A1 | 7/2008 | Tsuji et al. |
| 2009/0017441 A1 | 1/2009 | Peng et al. |

FOREIGN PATENT DOCUMENTS

| | | |
|---|---|---|
| CN | 1101982 | 4/1995 |
| CN | 1183559 | 6/1998 |
| CN | 1202621 | 12/1998 |
| CN | 1149397 | 5/2004 |
| EP | 0548983 | 6/1993 |
| EP | 0794435 | 9/1997 |
| WO | WO9717471 | 5/1997 |

OTHER PUBLICATIONS

Kristine M. Sovenyhazy et al., 'Spectroscopic Studies of the Multiple Binding Modes of a Trimethine-Bridged Cyanine Dye with DNA.' Necleic Acids Research, 2003, vol. 31 No. 10, pp. 2561-2569.

L.G.S. Brooker et al., 'Color and Constitution, VIII. Absorption of Unsymmetrical Carbocyanines.' Journal of the American Chemical Society, 1945, pp. 1889-1893.

Jason A. Bordelon et al., 'Viscometry and Atomic Force Microscopy Studies of the Interactions of a Dimeric Cyanine Dye with DNA.' J. Phys. Chem. B 2002, 106, 4838-4843.

Alexandre Frustenberg et al., 'Ultrafast Excited-State Dynamics of DNA Fluorescent Intercalators: New Insight into the Fluorescence Enhancement Mechanism.' J. Am. Chem. Soc. 2006, 128, 7661-7669.

Stephen J. Mason et al., 'Solid-Phase Catch, Activate, and Release Synthesis of Cyanine Dyes.' American Chemical Society Organic Letters, 2002, vol. 4 No. 24, pp. 4261-4264.

Notice of Allowance dated Aug. 7, 2009 for U.S. Appl. No. 11/967,991.

U.S. Appl. No. 12/482,335, filed Jun. 10, 2009, Shao Jianhui.

U.S. Appl. No. 12/580,474, filed Oct. 16, 2009, Yuji.

ASYMMETRIC CYANINE COMPOUNDS, THEIR PREPARATION METHODS AND THEIR USES

RELATED APPLICATIONS

This application claims priority to Chinese Patent Application No. 200810067815.6, filed Jun. 10, 2008, for "ASYMMETRIC CYANINE COMPOUNDS, THEIR PREPARATION METHODS AND THEIR USES," the disclosure of which is fully incorporated herein by reference.

TECHNICAL FIELD

The present disclosure relates to fluorescent dyes. More particularly, the present disclosure relates to asymmetric cyanine compounds useful in staining biological samples, compositions comprising the same and their use in staining biological samples.

BRIEF SUMMARY

Asymmetric cyanine compounds are disclosed. Conjugates and compositions comprising said asymmetric cyanine compounds and their use in staining biological samples are also disclosed.

DETAILED DESCRIPTION

Figure 1:
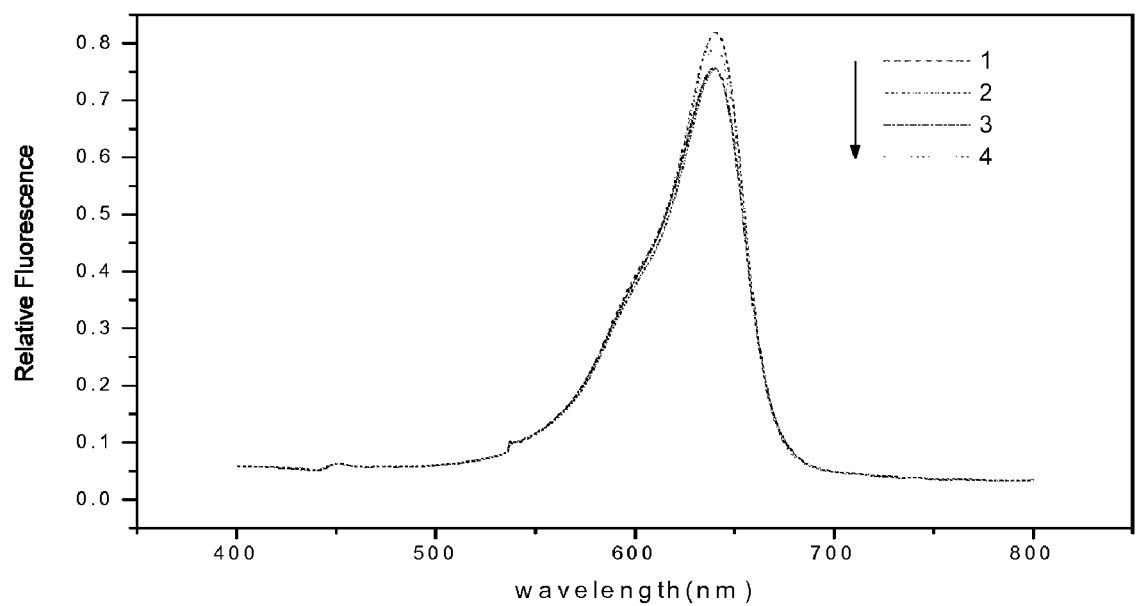
FIG. 1 is the absorption spectra for Dye-1 placed at different ambient temperatures for 48 hours.

Reticulocytes are transitional cells between the denucleated bone marrow intermediate and late erythroblasts, and the fully ripe erythrocytes. Subsequent to their release from bone marrow to peripheral blood, the reticulocytes, as they continue to mature into erythrocytes, show a gradual decrease in RNA content until complete disappearance of RNA in mature erythrocytes. Therefore, the intracellular RNA content represents the maturity of the reticulocytes. The assay of reticulocytes constitutes the fundamental test for evaluating the erythrocyte generation capability in hematological diagnosis and provides a basis for diagnosis of anemia, typing and detection of therapeutic efficacy, permitting the determination of the curative effects of the chemotherapy and transplantation of bone marrow as well as the therapeutic efficacy of EPO (erythropoietin).

Previous assays for reticulocytes generally involve manual microscopic inspection. As a result, the accuracy may be compromised by the plurality of steps in sample preparation and multiple artificial influencing factors, which generally cause an inter-operator variance up to 25% to 50%. With the development of flow cytometers, automatic equipment increases the correctness and precision in the detection of reticulocytes, and also provides reliable indicators on the maturity of the cells. However, the development of fluorescent dyes is fundamental to the advancement of fluorescence detection technologies, including, but not limited to, flow cytometers for detection of reticulocytes.

Early-used dyes include new methylene blue (NMB), brilliant cresyl blue (BCB), pyronin Y and ethidium bromide. They form complexes with nucleic acid molecules through intercalation or electrostatic attraction, and therefore enhanced fluorescence can be observed under a microscope. However, these dyes can form dye complexes by themselves that are not distinctly different from the complexes formed with nucleic acids, resulting in strong background interference in fluorescence. Also, these dyes have a low fluorescence quantum efficiency, which decreases the degree of fluorescent enhancement and affects the accuracy of detection results.

Acridine orange is also used in fluorescent analysis by virtue of the fluorescence-enhancing complexes that it forms with nucleic acids. However, these kinds of dye molecules may cause optical quenching among each other in the process of energy transfer, which results in the dye-nucleic acid complexes emitting no fluorescence and therefore influences the authenticity of detection results. Acridine orange may also have a strong interaction with the plastic tubes in flow cytometers, leading to increased intensity of background fluorescence. A longer time of washing of the tubes in the instruments is required for cleaning the post-detection residual dyes and ensuring the accuracy of detection results, and thus reducing the analysis efficiency of the instruments.

U.S. Pat. No. 4,957,870 discloses a thiazole blue dye useful in the detection of nucleic acids and blood reticulocytes. The excitation wavelength of this type of dye is at 488 nm, which requires a costly laser as the light source, and therefore increases the cost in equipment. Moreover, such a dye requires a long incubation time to better bind to nucleic acids.

One method of assaying cells with a flow cytometer involves the use of a red semiconductor laser. The red semiconductor laser can emit light at a wavelength of 633 nm at an ambient temperature of around 10° C. The wavelength of light, however, will change during operation with changes in ambient temperatures. Throughout the steady operation of the equipment, the ambient temperature will reach a temperature of 40° C. where the wavelength of the laser would accordingly increase to around 640 nm, which does not match well with the maximum absorption peak of the fluorescent dye, leading to a drop in the accuracy of the detection results. As a result, a thermostat must be attached to avoid the effect of temperature on the detection results. This can greatly increase the cost of the equipment.

Therefore, it would be desirable to develop novel compounds suitable for use as a fluorescent dye, which may include one or more of the following attributes: (1) emit little or no fluorescence when unbound to nucleic acids, but having a rapidly increased fluorescent intensity upon binding to nucleic acids with the light spectrum located in the near-infrared region so that interference from background fluorescence can be avoided; (2) capable of being excited at about 640 nm, with the wavelength remaining stable at 40° C. to match the working wavelength of the semiconductor laser used; or (3) showing some degree of specific binding to RNA.

In one embodiment there is provided a compound having the structure of the following general formula I:

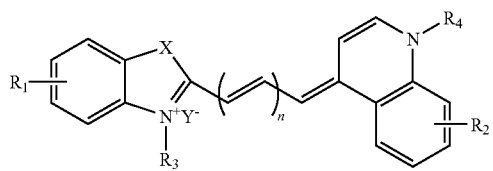

wherein n is 1, 2 or 3;

X is $C(CH_3)_2$, O, S or Se;

$R_1$ and $R_2$ are each independently selected from at least one of the following: H, a halogen and $C_{1-18}$alkylsulfo, provided that $R_1$ and $R_2$ are not simultaneously H;

$R_3$ and $R_4$ are each independently selected from at least one of the following: $C_{1-18}$alkyl and $C_{1-18}$alkyl$OR_5$, provided that $R_3$ and $R_4$ are not simultaneously alkyls when $R_2$ is a halogen;

$R_5$ is a hydrogen atom, acyl or lower alkyl; and $Y^-$ is an anion.

In another aspect there is provided a conjugate comprising a compound of the above formula I.

In yet another aspect there is provided a composition useful in staining biological samples, said composition comprising the compounds of the above formula I or conjugates thereof.

In still another aspect there is provided the use of a compound of the above formula I or conjugates or compositions thereof for staining biological samples.

In still a further aspect there is provided a method for analyzing reticulocytes, said method comprising staining the blood sample to be tested with a compound of the above formula I or conjugate or composition thereof and subjecting the stained blood sample to analysis in a flow cytometer to detect the reticulocytes.

In yet a further aspect there is provided a kit for analyzing reticulocytes, said kit comprising a compound of the above formula I or conjugate or composition thereof.

The compounds disclosed in the present disclosure may stain biological samples such as nucleic acids, erythroblasts, reticulocytes and the like, and the complexes thus formed have an emission wavelength in the near-infrared region, which avoids the interference from background fluorescence of the organisms per se, improves the accuracy of detection results and permits their use on a flow cytometer as the staining agent for various biological samples.

These and other features of the present disclosure will become apparent with reference to the following detailed description, including the drawings and the accompanying claims.

DEFINITIONS

Unless otherwise specified, the following terms as used herein have the following meanings.

The term "alkyl" as used herein individually or in combination with other groups refers to straight or branched alkyl groups containing 1-18 carbon atoms, such as 1-12, or alternatively 1-8, or 1-6 carbon atoms. Reference to a single alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The like rules also apply to other groups as used throughout the present specification.

As used herein, the term "lower alkyl" has the conventional meaning as used in the art and refers generally to $C_{1-6}$alkyl.

The term "acyl" as used herein refers to "alkyl", as defined above, attached to the group —CO—, wherein said "alkyl" contains 1-18 carbon atoms, such as 1-12, or alternatively 1-8, or 1-6 carbon atoms, such as formyl, acetyl, propionyl etc.

The term "halogen" as used herein includes fluorine, chlorine, bromine and iodine.

The term "biological sample" as used herein includes, but is not limited to, nucleic acids, erythroblasts and reticulocytes in the blood.

As used in this specification and the appended claims, the singular forms "a", "an", and "the" include plural references unless the context clearly dictates otherwise. Thus for example, a reference to "a compound" includes one or more compounds.

The word "comprise," and variations such as "comprises" and "comprising," will be understood to imply the inclusion of a stated integer or step or group of integers but not to the exclusion of any other integer or step or group of integers or steps.

Exemplary Compounds

In one embodiment a compound has the structure of the following general formula I:

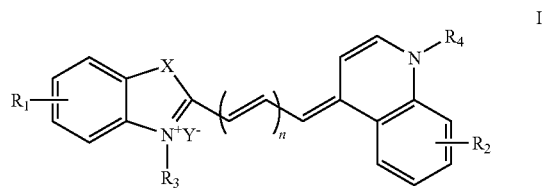

wherein n is 1, 2 or 3;

X is $C(CH_3)_2$, O, S or Se;

$R_1$ and $R_2$ are each independently selected from at least one of the following: H, a halogen and $C_{1-18}$alkylsulfo, provided that $R_1$ and $R_2$ are not simultaneously H;

$R_3$ and $R_4$ are each independently selected from at least one of the following: $C_{1-18}$alkyl and $C_{1-18}$alkylOR$_5$, provided that $R_3$ and $R_4$ are not simultaneously alkyls when $R_2$ is a halogen;

$R_5$ is a hydrogen atom, acyl or lower alkyl;

$Y^-$ is an anion.

In one embodiment $R_1$ and $R_2$ are each independently selected from at least one of the following: H, halogen, and $C_{1-6}$alkylsulfo, provided that $R_1$ and $R_2$ are not simultaneously H;

In one embodiment $R_3$ is $C_{1-6}$alkyl or $C_{1-6}$alkylOR$_5$.

In one embodiment $R_4$ is $C_{1-6}$alkyl or $C_{1-6}$alkylOR$_5$.

In one embodiment $R_5$ is H, $C_{1-3}$alkylCO or $C_{1-6}$alkyl.

In one embodiment X is $C(CH_3)_2$, O or S.

In one embodiment n is 1 or 2.

In one embodiment $Y^-$ is a halogen ion, $ClO_4^-$, $PF_6^-$, $CF_3SO_3^-$, $BF_4^-$, acetate or p-toluenesulfonate anions.

In one embodiment, a compound of formula I is selected from Dye-1, Dye-2, Dye-3, Dye-4, Dye-5 or Dye-6, wherein such dyes have the following structures:

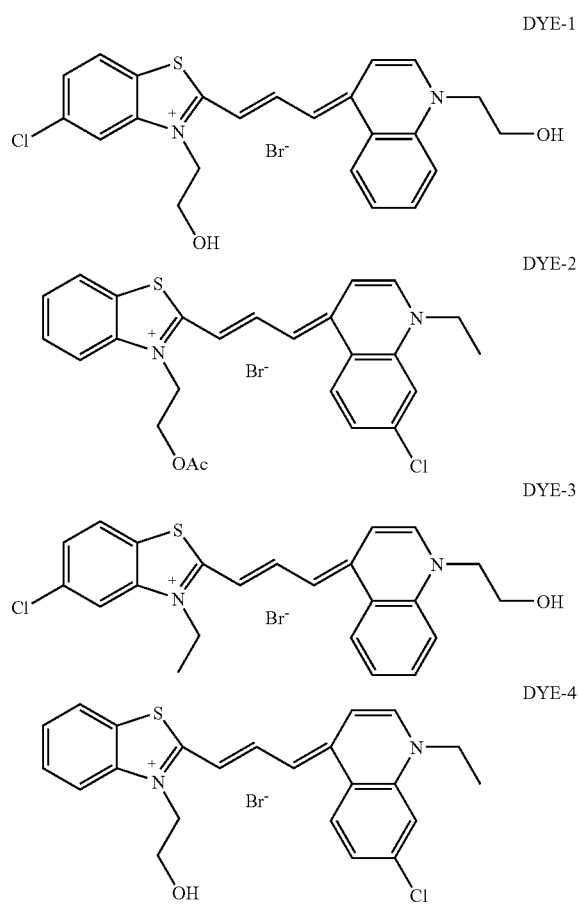

-continued

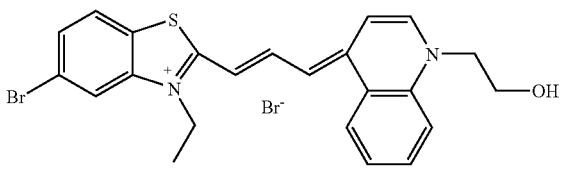

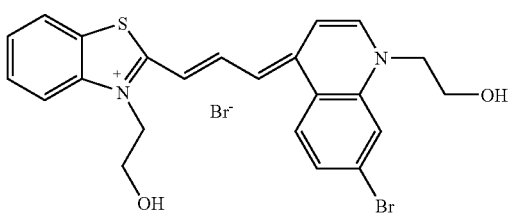

The compounds disclosed herein can be directly used for staining biological samples in the form of salts as described herein. Alternatively, in one embodiment, the compounds disclosed herein can exist in the form of derivatives of the compounds of formula I, said derivatives including, but not limited to, conjugates.

Typically, conjugates are used in the fluorescence activated cell sorter (FACS). "Conjugates" as used herein refer to the compounds formed by attaching the compounds disclosed herein to other molecules via covalent bonds. Molecules that can be conjugated with the compounds disclosed may be those that specifically bind to cells or cell components, including, but not limited to, antibodies, antigens, receptors, ligands, enzymes, substrates, coenzymes or the like. Generally, the test sample is incubated with the fluorescent conjugates for a period of time so that the fluorescent conjugates bind specifically to certain cells or cell components in the test sample. The binding of the fluorescent conjugates to the cells or cell components is also referred to as staining. The staining step can be repeated in sequence several times, or a variety of conjugates can be used for concurrent multistaining. After staining, analysis of the sample is conducted in the fluorescence activated cell sorter, wherein the excitation light source excites the fluorescent dyes disclosed herein within the conjugates and the detection apparatus then detects the emitted light generated by the excited fluorescent dyes.

Alternatively, in another embodiment, the fluorescent conjugates can be used in solid phase immunological assays, e.g., in sandwich immunological assays. The techniques for solid phase immunological assays are well known in the art and can be found in standard textbooks. The fluorescent conjugates disclosed herein can be used as various suitable components in solid phase immunological assays.

Methods for Preparing Exemplary Compounds

The compounds disclosed herein can be prepared using general methods known in the art. See, for example, Chinese Patent Application CN200710137258.6, which is incorporated herein by reference. In particular, the asymmetric cyanine compounds disclosed herein are generally synthesized by the following steps. First, unsubstituted or substituted 2-methylbenzothiazole, 2-methylbenzoxazole or 2,3,3-trimethyl-3H-indoline or the like as the starting material is reacted with a halide of formula $R_3X$ (X is F, Cl, Br or I) in a molar ratio of 1:1-2 by refluxing in toluene for 12-36 hours to obtain the quaternary ammonium salt intermediates of formula II:

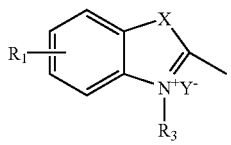

II wherein X, $R_1$, $R_3$ and $Y^-$ are as defined in the compounds of the above formula I.

Next, the resulting quaternary ammonium salt intermediates of formula II are condensed with linking molecules to obtain the compounds of formula III:

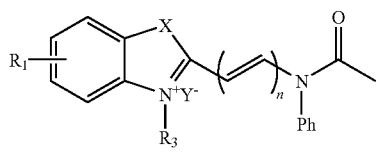

III wherein X, n, $R_1$, $R_3$ and $Y^-$ are as defined in the compounds of formula I, and the linking molecules can be N,N'-diphenylformamidine or higher homologues thereof.

Then, substituted or unsubstituted 4-methylquinolinium salt intermediates are obtained in a process similar to that used in the synthesis of the compounds of formula II. Finally, the 4-methylquinolinium salt intermediates are refluxed with the compounds of formula III in pyridine or acetic anhydride to obtain the fraction containing the desired asymmetric cyanine compounds. The resulting compounds can be recovered using separation and purification techniques well known in the art to achieve the desired purity.

The raw materials used in the present disclosure are commercially available, or can be readily prepared from raw materials known in the art using methods known to those skilled in the art or methods disclosed in the prior art.

The fluorescent conjugates comprising the compounds of formula I can be synthesized using any conventional methods known in the art.

Exemplary Compositions

The present disclosure also provides compositions comprising the above-mentioned compounds of formula I or conjugates thereof, said compositions being useful for staining biological samples.

The compositions may comprise, besides the compounds of formula I or conjugates thereof, other components required for staining biological samples, including, but not limited to, solvents, osmotic regulating agents, pH regulating agents, or surfactants. The compositions may exist in the form of an aqueous solution, or in other suitable forms that can be formulated into solution using water prior to usage.

Usage of the Exemplary Compounds or Compositions

The present disclosure further provides a method for staining biological samples using the above-mentioned compounds of the formula I or conjugates thereof, or compositions comprising the above-mentioned compounds of formula I or conjugates thereof. The method may include the step of contacting the above-mentioned compounds of formula I or conjugates thereof, or the compositions comprising the above-mentioned compounds of formula I or conjugates thereof with the biological samples. The term "contacting" as used herein may include contacting in solution or in solid phase.

The present disclosure also provides a method for analyzing reticulocytes, said method comprising obtaining a compound of the above formula I, or a conjugate or composition including the compound; staining a blood sample with such a compound, conjugate or composition, subjecting the treated blood sample to analysis in a flow cytometer and detecting the reticulocytes.

The present disclosure further provides a kit for analyzing reticulocytes, said kit comprising a compound of the above formula I, or a conjugate or a composition thereof.

Characteristics

From the above description and common knowledge familiar to those skilled in the art, the various characteristics of the asymmetric cyanine compounds disclosed may include, but are not limited to the following: (1) a maximum excitation wavelength of about 640 nm, which may not change with temperature and which matches the wavelength of the red semiconductor laser used; (2) when forming a complex with a nucleic acid, the dye/nucleic acid complex has an emission wavelength in the range of 600 nm to 900 nm in the near-infrared region, which avoids interference from the background fluorescence of the organisms per se and helps to improve the accuracy of detection results; (3) the ability to specifically stain RNA to some degree; or (4) the ability to be used in a flow cytometer as a staining agent for blood reticulocytes.

EXAMPLES

The present disclosure is further illustrated by the following particular examples to which or by which the present disclosure is not limited, as is appreciated by one skilled in the art.

Example 1

Synthesis of 4-methyl-7-chloroquinoline 32.8 g. (0.2 mol) 3-chloroaniline hydrochloride, 81 g. ferric trichloride hexahydrate (0.3 mol), 3.0 g. redried anhydrous zinc chloride and 150 mL 95% ethanol were added into a 500 mL 3-neck flask equipped with a reflux condenser, a magnetic stirrer with heating, a thermometer and a constant-pressure dropping funnel, and the mixture was stirred and heated to 60° C. 12.6 g. (0.18 mol) methyl vinyl ketone was added slowly through the constant-pressure dropping funnel while maintaining the temperature at 60-70° C., followed by raising the temperature to reflux for 2 hours. After cooling, the mixed solution was added with 25% aqueous sodium hydroxide until alkaline. The solvent was then distilled off under reduced pressure until dry. The resulting solids were removed and repeatedly extracted with anhydrous ethyl ether. The extracts were collected, dried over anhydrous potassium carbonate and filtered. After removing the solvent, the residue was purified in a silica column using hexane/ethyl acetate (3:1) as the mobile phase to afford 11.38 g. of product.

Example 2

Synthesis of 4-methyl-7-bromoquinoline

The title compound was obtained in a similar method for synthesizing 4-methyl-7-chloroquinoline with the exception that 3-bromoaniline was substituted for 3-chloroaniline as a starting material.

Example 3

Synthesis of Dye-1

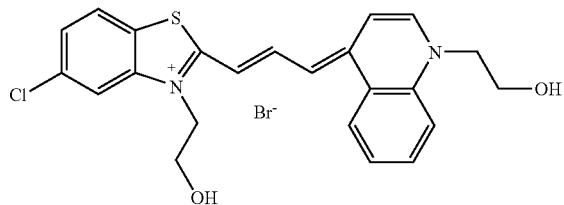

In a mixed solution of 40 mL of methanol and 20 mL of ethanol, 10 mmol of 5-chloro-3-(2-hydroxyethyl)-2-methyl-benzothiazolium bromide and 30 mmol of N,N'-diphenylformamidine were heated while stirring in a 65° C. oil bath for 6 hours. After the reaction was completed, the solvents were distilled off under reduced pressure. Then a certain amount of ethyl ether was added and the mixture was stirred to precipitate out orange solid powder which was then filtered and dried. The crude product was recrystallized in ethyl acetate-hexane to obtain an orange-red solid product with a yield of 41%. Into 4.0 mmol of the obtained reaction product were added 4.2 mmol of 1-(2-hydroxyethyl)-4-methylquinolinium bromide and 10 ml of pyridine, and the mixture was heated while stirring in a 90° C. oil bath for 1.5 hours. The reaction was cooled down to room temperature and then poured into ethyl ether to precipitate out dark purple-red solids which were then filtered and dried. The dye was separated through a silica column using dichloromethane:methanol=100:0→100:15 as the gradient eluent. The blue fractions were collected and subjected to rotary evaporation to remove the solvents. The residue was then dried in a vacuum drying oven at 45° C. for 24 hours to obtain the exemplary Dye-1 compound in a yield of 49%.

Maximum absorption peak: 638 nm (methanol/ethylene glycol)

MS (EI) $C_{23}H_{22}BrClN_2O_2S$ m/z: 425.9 $[M-Br]^+$.

Example 4

Synthesis of Dye-2

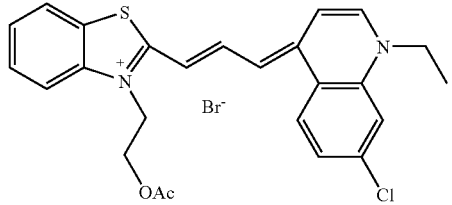

In 60 mL of acetic anhydride, 10 mmol of 3-(2-hydroxyethyl)-2-methylbenzothiazolium bromide and 30 mmol of N,N'-diphenylformamidine were heated while stirring in a 90° C. oil bath for 4 hours. After cooling the reaction to room temperature, the resulting red oily matter was washed in suspension in 1.5 L of petroleum ether 3 times to thoroughly remove acetic anhydride. Then a certain amount of ethyl ether was added and the mixture was stirred to precipitate out orange solid powder which was then filtered and dried. The crude product was purified through a silica column (dichloromethane:methanol=100:5) to afford an orange-red solid product with a yield of 58%. Into 4.0 mmol of the obtained reaction product were added 4.2 mmol of 7-chloro-1-ethyl-4-methylquinolinium bromide and 10 ml of acetic anhydride, and the mixture was heated while stirring in a 90° C. oil bath for 1.5 hours. The reaction was poured into ethyl ether to precipitate out small dark purple particles which were then filtered and dried. The dye was separated through a silica column using dichloromethane:methanol=100:0→100:9 as the gradient eluent. The blue fractions were collected and subjected to rotary evaporation to remove the solvents. The residue was then dried in a vacuum drying oven at 45° C. for 24 hours to obtain the exemplary Dye-2 compound in a yield of 53%.

Maximum absorption peak: 639 nm (methanol/ethylene glycol)

MS (EI) $C_{25}H_{24}BrClN_2O_2S$ m/z: 451.9 $[M-Br]^+$.

Example 5

Synthesis of Dye-3

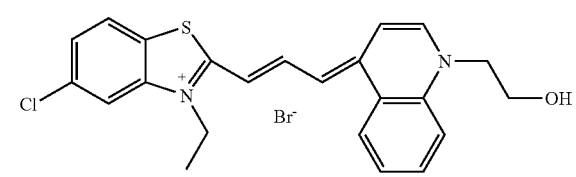

In 50 mL of acetic acid solution, 10 mmol of 5-chloro-3-ethyl-2-methylbenzothiazolium bromide and 30 mmol of N,N'-diphenylformamidine were heated while stirring in a 65° C. oil bath for 1.5 hours. After cooling the reaction to room temperature, the resulting red oily matter was washed in suspension in 1.5 L of petroleum ether 3 times to thoroughly remove acetic acid. Then a certain amount of ethyl ether was added and the mixture was stirred to precipitate out orange solid powder which was then filtered and dried. The crude product was recrystallized in ethyl acetate-hexane to obtain an orange-red solid product with a yield of 47%. Into 4.0 mmol of the obtained reaction product were added 4.2 mmol of 1-(2-hydroxyethyl)-4-methylquinolinium bromide and 10 ml of pyridine, and the mixture was heated while stirring in a 90° C. oil bath for 1.5 hours. The reaction was cooled down to room temperature and then poured into ethyl ether to precipitate out purple-red solids which were then filtered and dried. The dye was separated through a silica column using dichloromethane:methanol=100:0→100:10 as the gradient eluent. The blue fractions were collected and subjected to rotary evaporation to remove the solvents. The residue was then dried in a vacuum drying oven at 45° C. for 24 hours to obtain the exemplary Dye-3 compound in a yield of 40%.

Maximum absorption peak: 640 nm (methanol/ethylene glycol)

MS (EI) $C_{23}H_{22}BrClN_2OS$ m/z: 409.9 $[M-Br]^+$.

Example 6

Synthesis of Dye-4

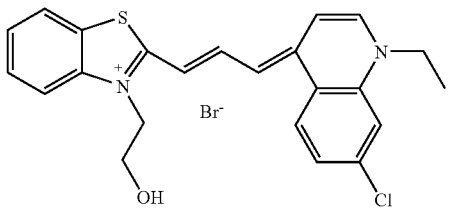

In a mixed solution of 40 mL of methanol and 20 mL of ethanol, 10 mmol of 3-(2-hydroxyethyl)-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then a certain amount of ethyl ether was added and the mixture was stirred to precipitate out orange solid powder which was then filtered and dried. The crude product was recrystallized in ethyl acetate-hexane to obtain an orange-red solid product with a yield of 44%. Into 4.0 mmol of the obtained reaction product were added 4.2 mmol of 7-chloro-1-ethyl-4-methylquinolinium bromide and 10 ml of pyridine, and the mixture was heated while stirring in a 90° C. oil bath for 1.5 hours. The reaction was cooled down to room temperature and then poured into ethyl ether to precipitate out dark purple-red solids which were then filtered and dried. The dye was separated through a silica column using dichloromethane:methanol=100:0→100:8 as the gradient eluent. The blue fractions were collected and subjected to rotary evaporation to remove the solvents. The residue was then dried in a vacuum drying oven at 45° C. for 24 hours to obtain the exemplary Dye-4 compound in a yield of 58%.

Maximum absorption peak: 639 nm (methanol/ethylene glycol)

MS (EI) $C_{23}H_{22}BrClN_2OS$ m/z: 409.9 $[M-Br]^+$.

Example 7

Synthesis of Dye-5

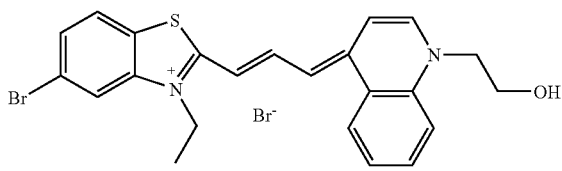

In 50 mL of acetic acid solution, 10 mmol of 5-bromo-3-ethyl-2-methylbenzothiazolium bromide and 30 mmol of N,N'-diphenylformamidine were heated while stirring in a 65° C. oil bath for 1.5 hours. After cooling the reaction to room temperature, the resulting red oily matter was washed in suspension in 1.5 L of petroleum ether 3 times to thoroughly remove acetic acid. Then a certain amount of ethyl ether was added and the mixture was stirred to precipitate out orange solid powder which was then filtered and dried. The crude product was recrystallized in ethyl acetate-hexane to obtain an orange-red solid product with a yield of 50%. Into 4.0 mmol of the obtained reaction product were added 4.2 mmol of 1-(2-hydroxyethyl)-4-methylquinolinium bromide and 10 ml of pyridine, and the mixture was heated while stirring in a 90° C. oil bath for 1.5 hours. The reaction was cooled down to room temperature and then poured into ethyl ether to precipitate out purple-red solids which were then filtered and dried. The dye was separated through a silica column using dichloromethane:methanol=100:0→100:15 as the gradient eluent. The blue fractions were collected and subjected to rotary evaporation to remove the solvents. The residue was then dried in a vacuum drying oven at 45° C. for 24 hours to obtain the exemplary Dye-5 compound in a yield of 46%.

Maximum absorption peak: 640 nm (methanol/ethylene glycol)

MS (EI) $C_{23}H_{22}Br_2N_2OS$ m/z: 454.4 $[M-Br]^+$.

Example 8

Synthesis of Dye-6

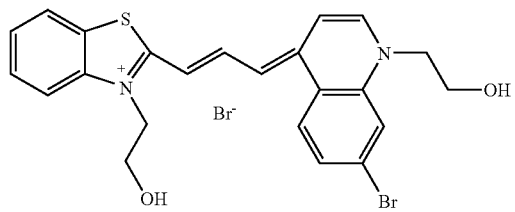

In a mixed solution of 40 mL of methanol and 20 mL of ethanol, 10 mmol of 3-(2-hydroxyethyl)-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then a certain amount of ethyl ether was added and the mixture was stirred to precipitate out orange solid powder which was then filtered and dried. The crude product was recrystallized in ethyl acetate-hexane to obtain an orange-red solid product with a yield of 41%. Into 4.0 mmol of the obtained reaction product were added 4.2 mmol of 7-bromo-1-(2-hydroxyethyl)-4-methylquinolinium bromide and 10 ml of pyridine, and the mixture was heated while stirring in a 90° C. oil bath for 1.5 hours. The reaction was cooled down to room temperature and then poured into ethyl ether to precipitate out dark purple-red solids which were then filtered and dried. The dye was separated through a silica column using dichloromethane:methanol=100:0→100:20 as the gradient eluent. The blue fractions were collected and subjected to rotary evaporation to remove the solvents. The residue was then dried in a vacuum drying oven at 45° C. for 24 hours to obtain the exemplary Dye-6 compound in a yield of 49%.

Maximum absorption peak: 638 nm (methanol/ethylene glycol)

MS (EI) $C_{30}H_{22}Br_2N_2O_2S$ m/z: 470.4 $[M-Br]^+$.

Example 9

Detection of the Absorption Peak of the Fluorescent Dyes

A certain amount of an asymmetric cyanine compound was accurately weighed and sufficiently dissolved in 2.5 mL of methanol/ethylene glycol solution (50:50 vol/vol) to prepare a fluorescent dye solution at a concentration of 5 mM. Four parts of 5 μL aliquots of the fluorescent dye solution were each diluted in 2 mL of methanol/ethylene glycol solution (50:50 vol/vol) and were let stand under a hermetic and light-proof condition at 0° C., 20° C., 40° C. and 60° C. respectively for 48 hours. The maximum absorption peak was detected using a ultraviolet-visible spectrophotometer. The absorption peaks of Dye-3 after standing at different temperatures are shown in FIG. 1. It can be seen from the figure that the position of the maximum absorption peak of Dye-3 did not shift as a function of the temperature and thus best matched the excitation wavelength of the laser.

Table 1 shows the values of maximum absorption peak for Dye-1 to Dye-6 after standing at different temperatures for 48 hours.

TABLE 1

| Temperature | Maximum absorption peak of the compounds disclosed (nm) | | | | |
|---|---|---|---|---|---|
| | Dye-1 | Dye-2 | Dye-4 | Dye-5 | Dye-6 |
| 0° C. | 638 | 639 | 639 | 640 | 638 |
| 20° C. | 638 | 639 | 639 | 640 | 638 |
| 40° C. | 638 | 639 | 639 | 640 | 638 |
| 60° C. | 638 | 639 | 639 | 640 | 638 |

The data in the above table evidence the unchangeableness of the maximum absorption peak of the compounds disclosed after standing at different temperatures for 48 hours.

Example 10

Figure 2:
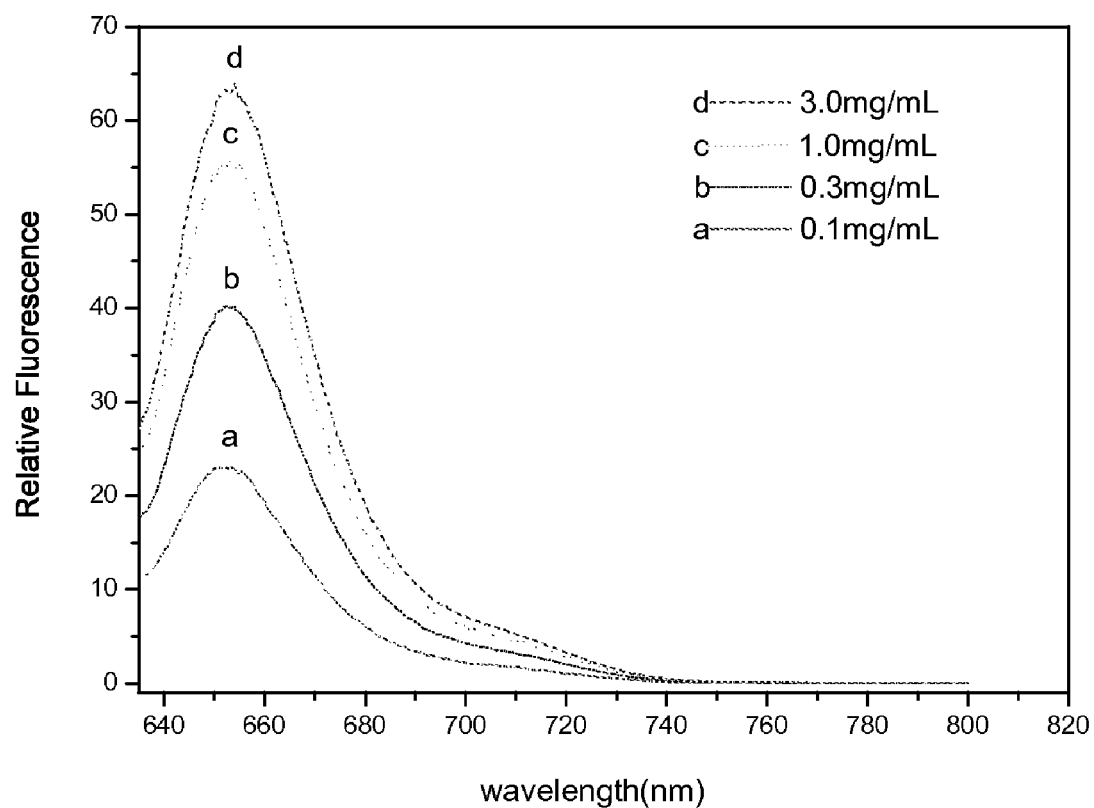
FIG. 2 is the fluorescence emission spectra for Dye-1 in phosphate buffered solution (PBS) after it binds with various concentrations of salmon sperm DNA.

Detection of the Fluorescence Intensity of Dye-1 in PBS Containing Different Concentrations of DNA A certain amount of Dye-1 was accurately weighed and sufficiently dissolved in 2.5 mL of methanol/ethylene glycol (50:50 vol/vol) to prepare a dye solution at a concentration of 5 mM. This solution was filtered before use. Separate amounts of salmon sperm DNA were weighed and dissolved in PBS to obtain PBS buffers containing 3 mg/mL, 1 mg/mL, 0.3 mg/mL, 0.1 mg/mL of DNA. 2 μL aliquots of the prepared 5 mM dye solution were accurately measured and respectively combined in 1 mL of PBS with 1 μL of the PBS buffers containing different concentrations of DNA. After reacting for a period of time, the complexes were detected for their emission spectra at the selected excitation wavelength (which the skilled artisan would understand is the maximum absorption wavelength of the dye. See, e.g., Table 1). The detection was performed at room temperature. The instrument used was fluorescence spectrophotometer Model FL-4500. The results are shown in FIG. 2. It can be seen from the figure that the fluorescence emission strength of the dye/DNA complexes increased rapidly with the increase in DNA concentration.

Figure 3:
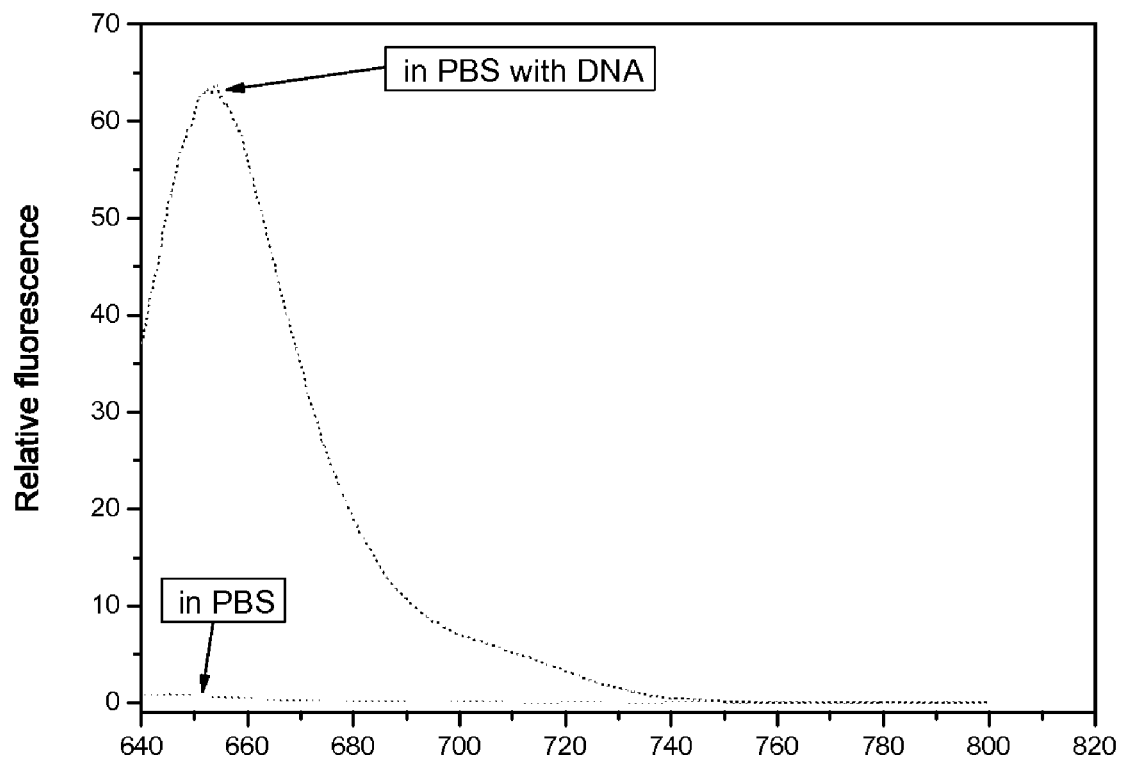
FIG. 3 is the fluorescence emission spectra for Dye-1 in PBS before and after it binds with salmon sperm DNA.

FIG. 3 is a comparison of the relative fluorescence strength of Dye-1 in PBS before and after it is bound with DNA. As can be seen from the figure, Dye-1 scarcely generated any fluorescence in PBS without DNA, but when it formed complexes with DNA, the fluorescence intensity increased rapidly, with the maximum excitation peak at about 660 nm that represented a relatively large Stoke's shift, which can avoid the interference from the background fluorescence and improve the accuracy of the detected signal.

Example 11

Figure 4:
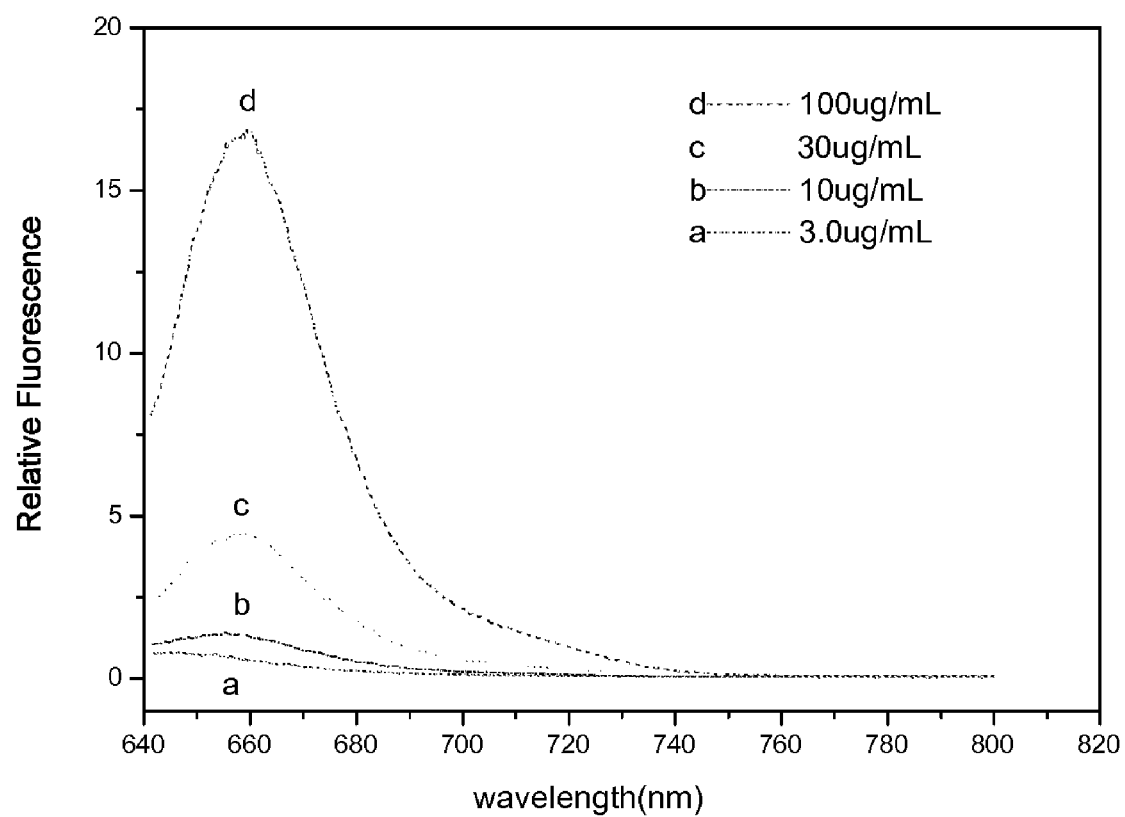
FIG. 4 is the fluorescence emission spectra for Dye-1 in PBS after it binds with various concentrations of soft-shelled turtle (*Trionyx sinensis*) liver RNA.

Detection of the Fluorescence Intensity of Dye-1 in PBS Containing Different Concentrations of RNA A certain amount of Dye-1 was accurately weighed and sufficiently dissolved in 2.5 mL of methanol/ethylene glycol (50:50 vol/vol) to prepare a dye solution at a concentration of 5 mM. This solution was filtered before use. Separate amounts of freshly prepared soft-shelled turtle (*Trionyx sinensis*) liver RNA were weighed and dissolved in PBS to obtain PBS buffers containing 100 μg/mL, 30 μg/mL, 10 μg/mL, 3 μg/mL of RNA. 2 μL aliquots of the prepared 5 mM dye solution were accurately measured and respectively combined in 1 mL of PBS with 1 μL of the PBS buffers containing different concentrations of RNA. After reacting for a period of time, the complexes were detected for their emission spectra at the selected excitation wavelength (which the skilled artisan would understand is the maximum absorption wavelength of the dye. See, e.g., Table 1). The detection temperature was at room temperature. The instrument used was fluorescence spectrophotometer Model FL-4500. The results are shown in FIG. 4. It can be seen from the figure that the fluorescence emission strength of the dye/RNA complexes increased rapidly with the increase in RNA concentration.

Figure 5:
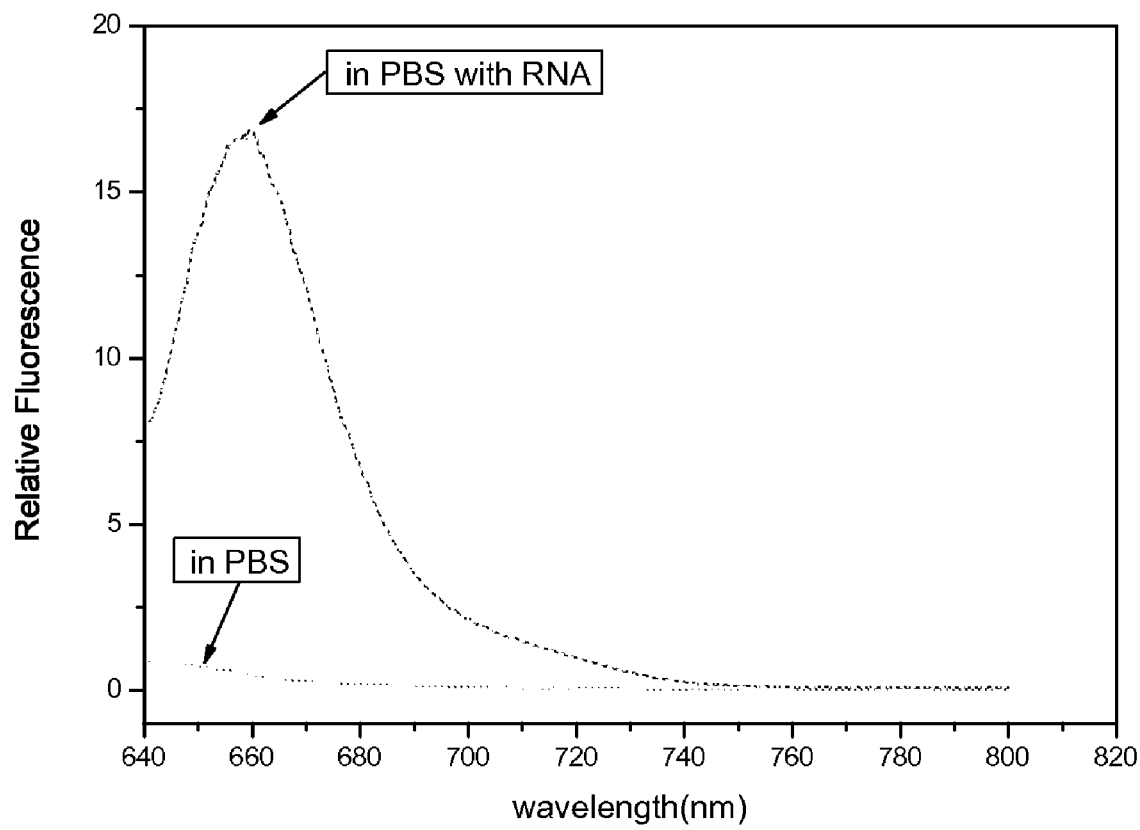
FIG. 5 is the fluorescence emission spectra for Dye-1 in PBS before and after it binds with soft-shelled turtle (*Trionyx sinensis*) liver RNA.

FIG. 5 is a comparison of the relative fluorescence strength of Dye-1 in PBS before and after it is bound with RNA. As can likewise be seen in the figure, when Dye-1 formed complexes with RNA, there occurred a rapid increase in fluorescence intensity accompanied by a certain degree of red shift of fluorescence, with the maximum excitation peak at about 660 nm in the near-infrared region, which can avoid the interference from the background fluorescence of the organisms per se and therefore improve the accuracy of detection.

Example 12

Figure 6:
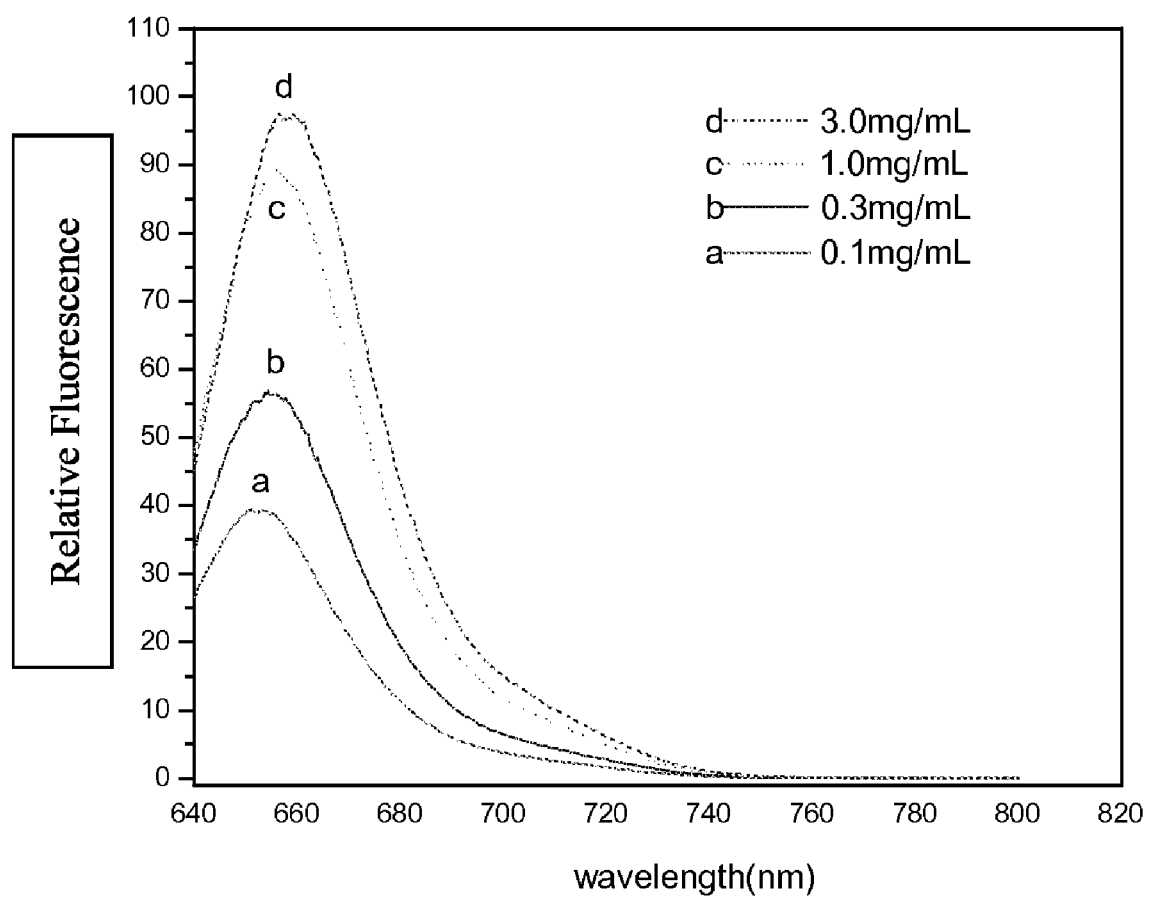
FIG. 6 is the fluorescence emission spectra for Dye-3 in PBS after it binds with various concentrations of salmon sperm DNA.
Figure 7:
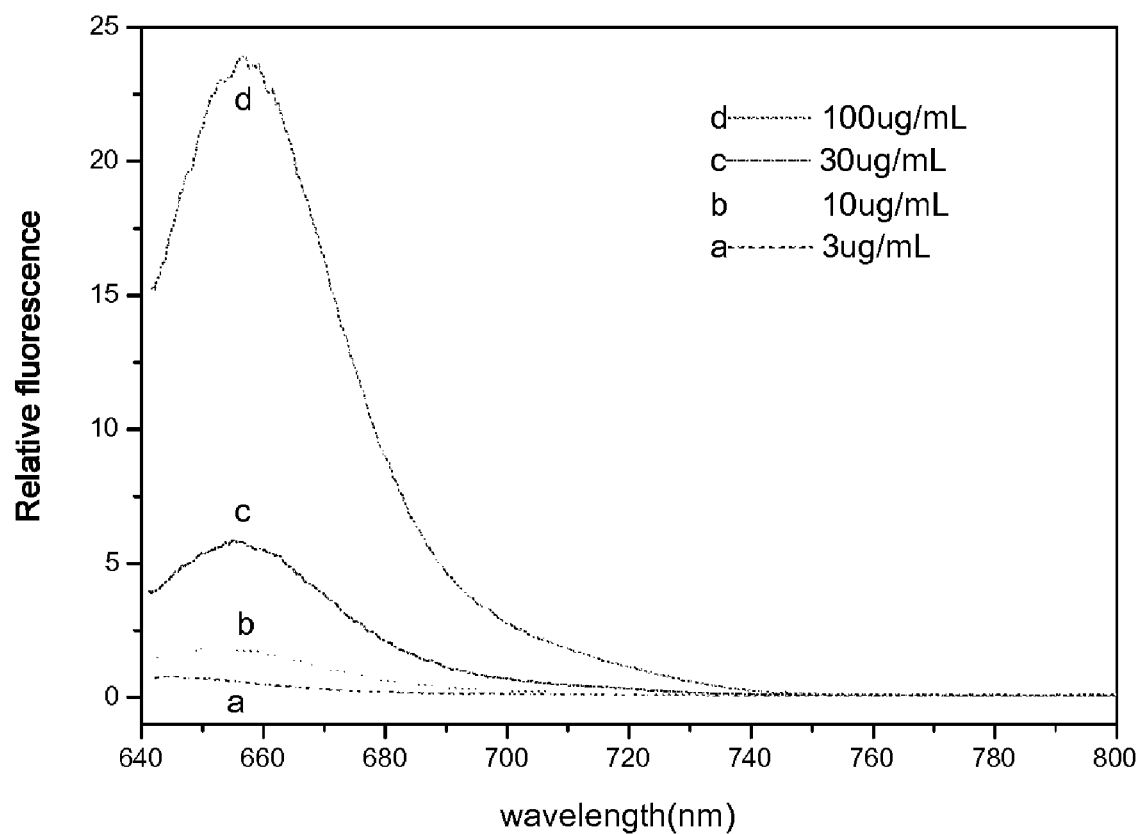
FIG. 7 is the fluorescence emission spectra for Dye-3 in PBS after it binds with various concentrations of soft-shelled turtle (*Trionyx sinensis*) liver RNA.
Figure 8:
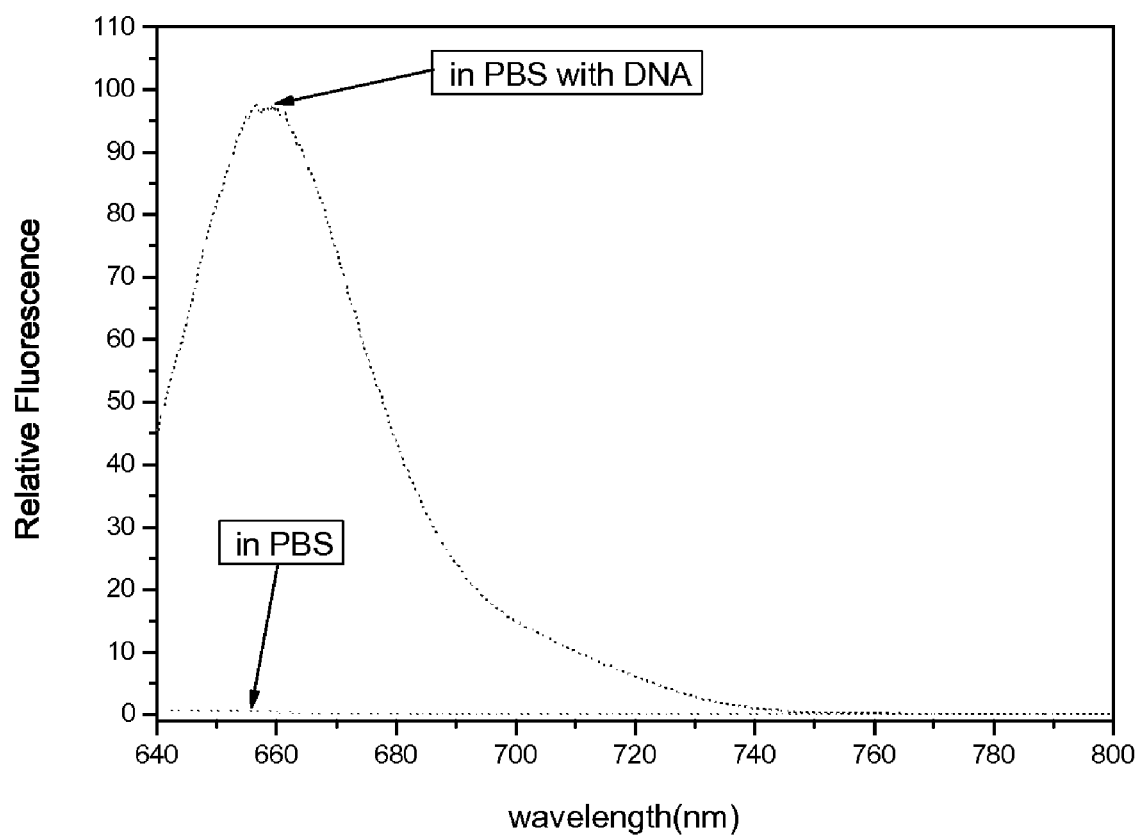
FIG. 8 is the fluorescence emission spectra for Dye-3 in PBS before and after it binds with salmon sperm DNA.
Figure 9:
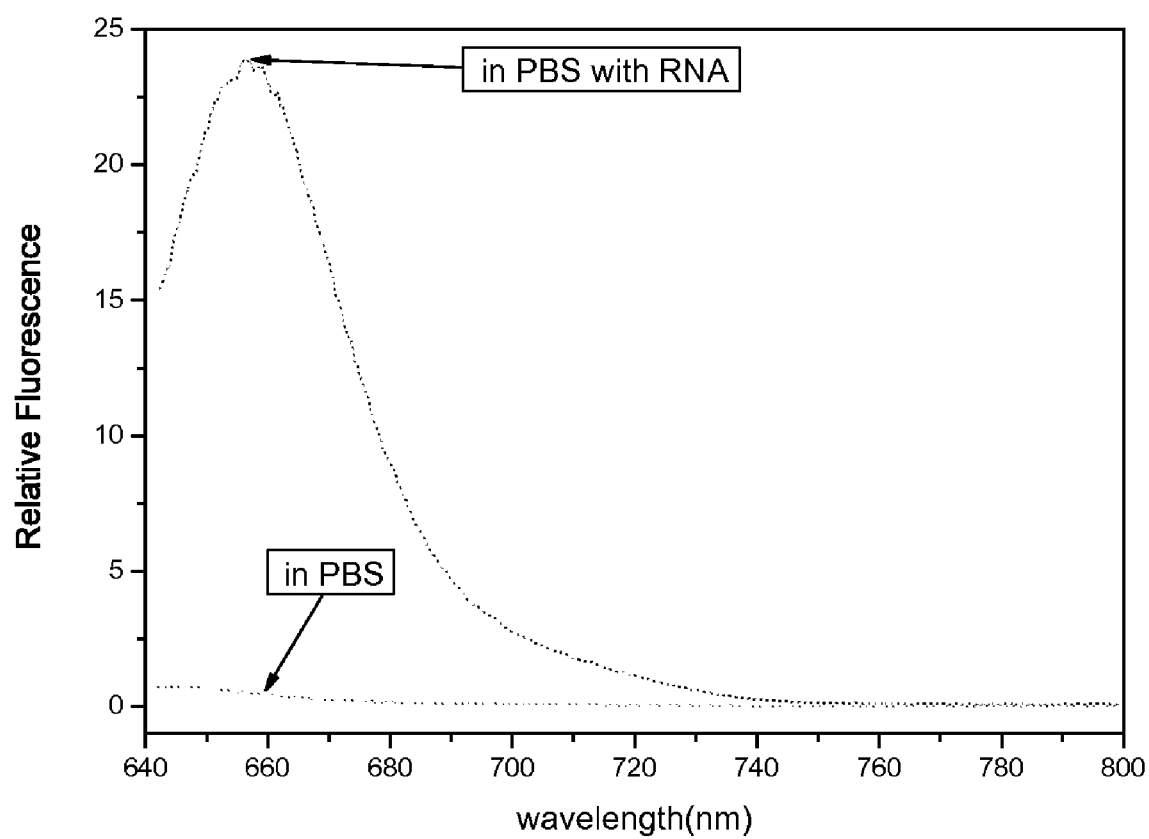
FIG. 9 is the fluorescence emission spectra for Dye-3 in PBS before and after it binds with soft-shelled turtle (*Trionyx sinensis*) liver RNA.

Detection of the Fluorescence Intensity of Dye-3 in PBS Containing Different Concentrations of DNA or of RNA The detection procedures followed were those described in Example 10 and Example 11. The fluorescence spectra for the complexes of Dye-3 and different concentrations of DNA or RNA are shown in FIG. 6 and FIG. 7, respectively. The comparisons of fluorescence intensity for Dye-3 before and after it is bound with DNA or with RNA in PBS are shown in FIG. 8 and FIG. 9, respectively. As can be seen from the figures, the dye per se scarcely generated any fluorescence, but when it formed complexes with the added nucleic acids, the fluorescence intensities likewise increased rapidly, with the maximum excitation peaks all beyond 655 nm in the near-infrared region.

Table 2 compares the ratios of increase in fluorescence intensity for Dye-1 and Dye-3 after they are bound with salmon sperm DNA in PBS with those before they are bound with salmon sperm DNA in PBS.

TABLE 2

| Dye | Relative fluorescence intensity | | Ratio of increase in fluorescence (after vs before binding) |
|---|---|---|---|
| | Before binding DNA | After binding DNA | |
| Dye-1 | 0.75 | 63.29 | 84 |
| Dye-3 | 0.67 | 97.56 | 146 |

Table 3 compares the ratios of increase in fluorescence for Dye-1 and Dye-3 after they are bound with soft-shelled turtle (*Trionyx sinensis*) liver RNA in PBS with those before they are bound with soft-shelled turtle (*Trionyx sinensis*) liver RNA in PBS.

TABLE 3

| Dye | Relative fluorescence intensity | | Ratio of increase in fluorescence (after vs before binding) |
|---|---|---|---|
| | Before binding RNA | After binding RNA | |
| Dye-1 | 0.75 | 16.79 | 22.4 |
| Dye-3 | 0.67 | 23.94 | 35.7 |

Example 13

Figure 10:
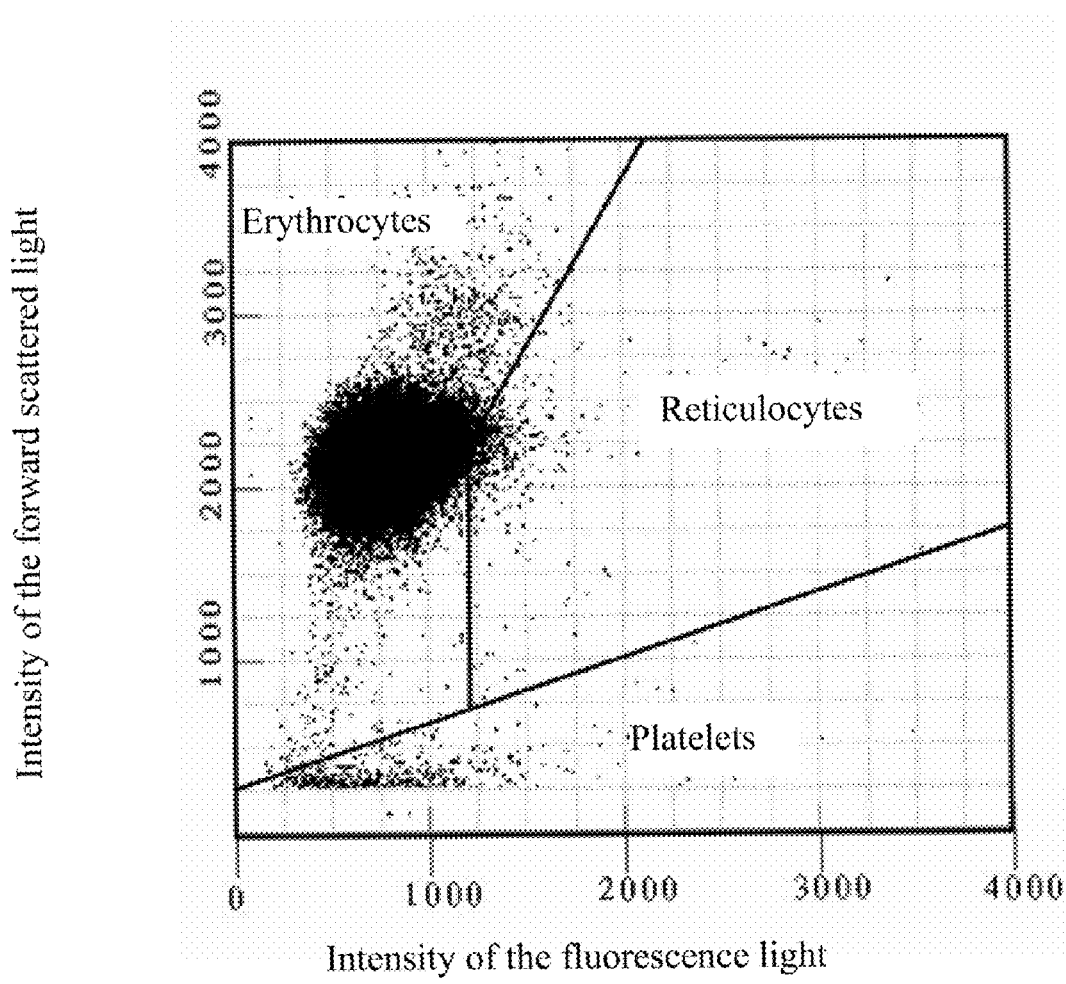
FIG. 10 is the scattergram showing the relationship between the intensity of forward scattered light and the intensity of fluorescence light when a blood sample is treated with the reagent comprising Dye-1 fluorescent dye for reticulocyte detection.

Dye-1 as a Reticulocyte Detection Reagent 10 uL of anticoagulant-treated blood was added into 2 mL of the Dye-1-containing reticulocyte detection reagent to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for the intensity of forward low-angle scattered light and fluorescence light. The reticulocytes were distinguished from other erythrocytes based on the fluorescence intensity and the scattered light intensity. The numbers of these two types of cells were counted and the cell ratio between them was calculated. FIG. 10 shows the comparison of the fluorescence of the reticulocytes with that of the total erythrocytes, with the reticulocytes comprising 0.26% of the total erythrocytes. The same anticoagulant-treated blood was detected using the method for the vital staining and microscopic counting of reticulocytes recommended by International Council for Standardization in Haematology (ICSH) and the result indicated that the reticulocytes comprised 0.25% of the total erythrocytes.

Example 14

Figure 11:
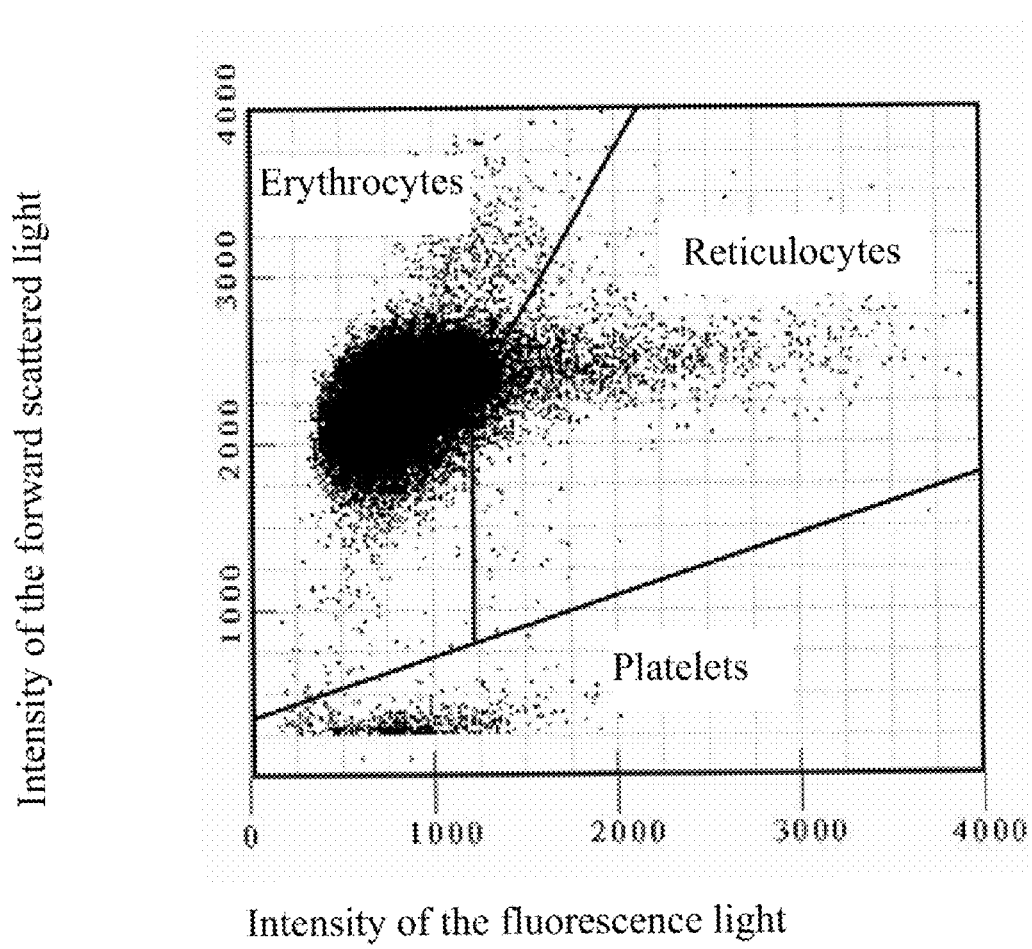
FIG. 11 is the scattergram showing the relationship between the intensity of forward scattered light and the intensity of fluorescence light when a blood sample is treated with the reagent comprising Dye-2 fluorescent dye for reticulocyte detection.

Dye-2 as a Reticulocyte Detection Reagent 10 uL of anticoagulant-treated blood was added into 2 mL of the Dye-2-containing reticulocyte detection reagent to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for the intensity of forward low-angle scattered light and fluorescence light. The reticulocytes were distinguished from other erythrocytes based on the fluorescence intensity and the scattered light intensity. The numbers of these two types of cells were counted and the cell ratio between them was calculated. FIG. 11 shows the comparison of the fluorescence of the reticulocytes with that of the total erythrocytes, with the reticulocytes comprising 1.91% of the total erythrocytes. The same anticoagulant-treated blood was detected using the method for the vital staining and microscopic counting of reticulocytes recommended by International Council for Standardization in Haematology (ICSH) and the result indicated that the reticulocytes comprised 1.89% of the total erythrocytes.

Example 15

Figure 12:
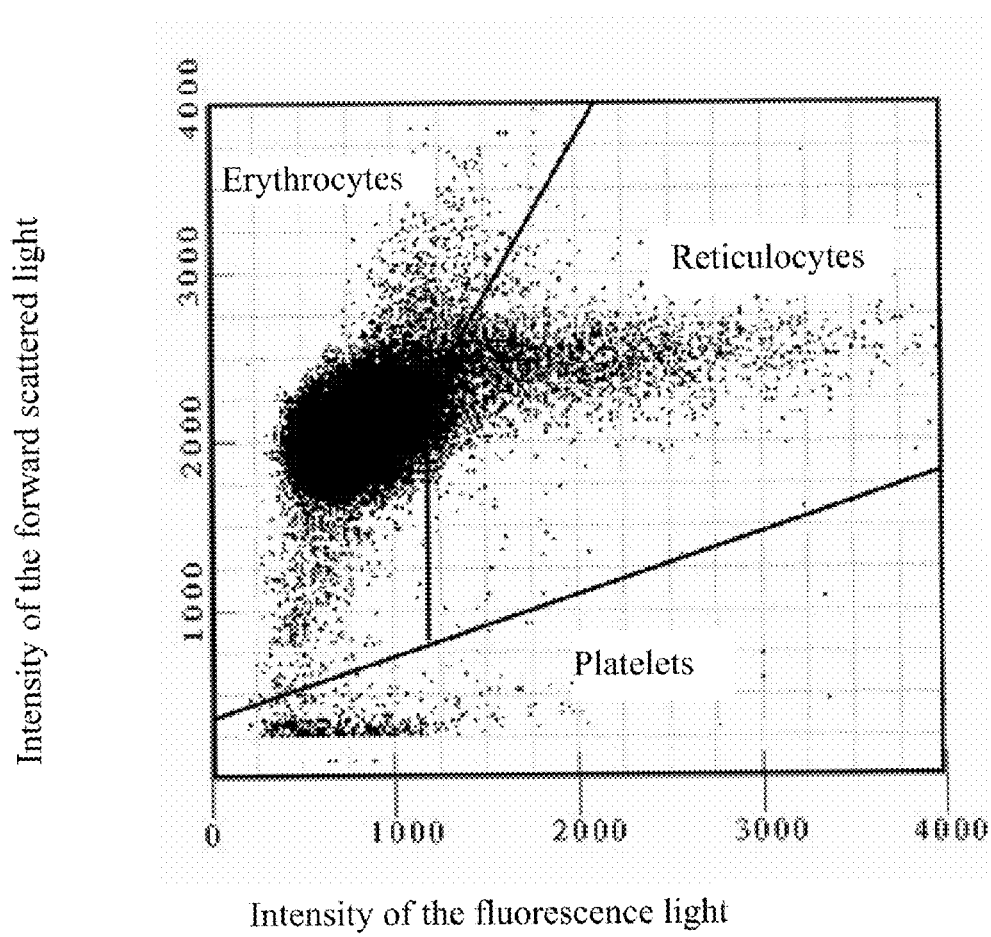
FIG. 12 is the scattergram showing the relationship between the intensity of forward scattered light and the intensity of fluorescence light when a blood sample is treated with the reagent comprising Dye-3 fluorescent dye for reticulocyte detection.

Dye-3 as a Reticulocyte Detection Reagent 10 uL of anticoagulant-treated blood was added into 2 mL of the Dye-3-containing reticulocyte detection reagent to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for the intensity of forward low-angle scattered light and fluorescence light. The reticulocytes were distinguished from other erythrocytes based on the fluorescence intensity and the scattered light intensity. The numbers of these two types of cells were counted and the cell ratio between them was calculated. FIG. 12 shows the comparison of the fluorescence of the reticulocytes with that of the total erythrocytes, with the reticulocytes comprising 3.0% of the total erythrocytes. The same anticoagulant-treated blood was detected using the method for the vital staining and microscopic counting of reticulocytes recommended by International Council for Standardization in Haematology (ICSH) and the result indicated that the reticulocytes comprised 3.05% of the total erythrocytes.

Example 16

Figure 13:
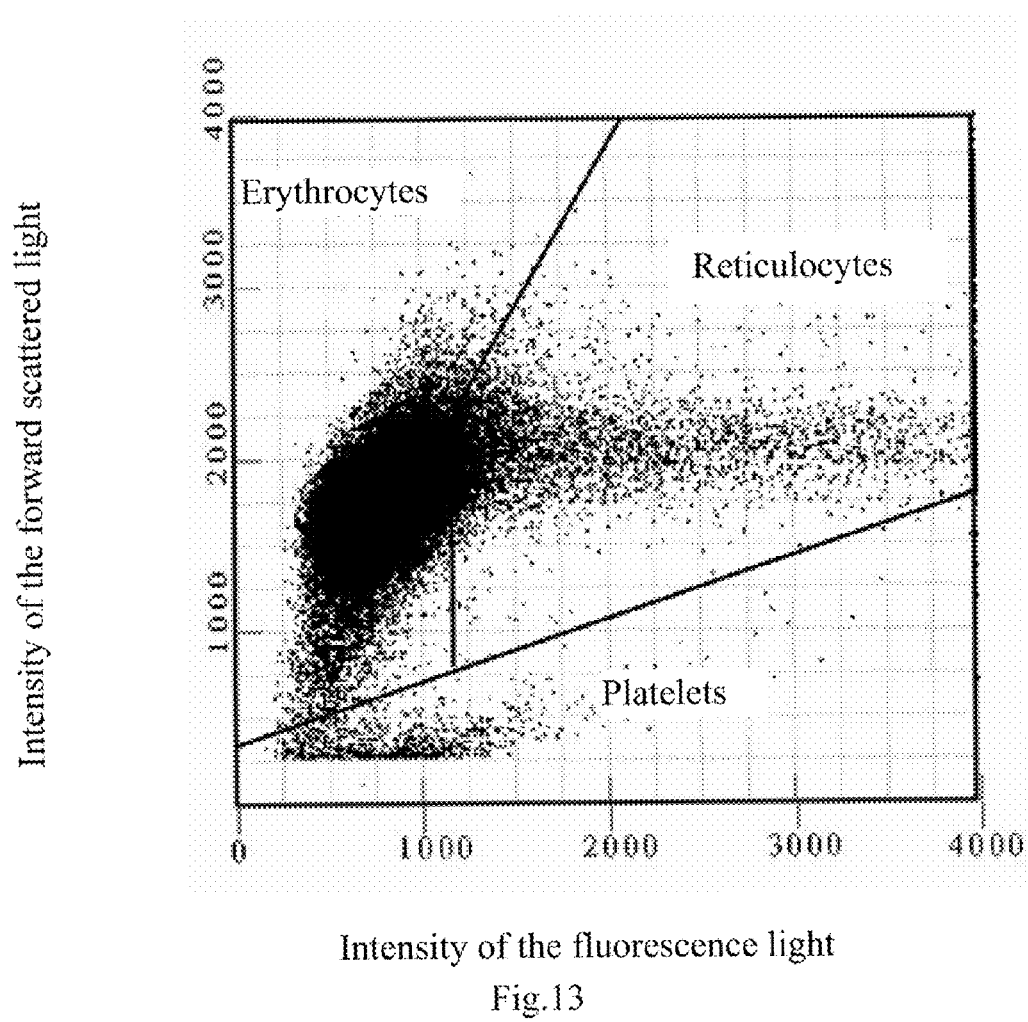
FIG. 13 is the scattergram showing the relationship between the intensity of forward scattered light and the intensity of fluorescence light when a blood sample is treated with the reagent comprising Dye-6 fluorescent dye for reticulocyte detection.

Dye-6 as a Reticulocyte Detection Reagent 10 uL of anticoagulant-treated blood was added into 2 mL of the Dye-6-containing reticulocyte detection reagent to prepare a test sample. Then the sample was sucked into the properly adapted flow cytometer (Chinese Patent CN 101000306A, Shenzhen Mindray Bio-medical Electronics Co., Ltd. Shenzhen, People's Republic of China) and detected for the intensity of forward low-angle scattered light and fluorescence light. The reticulocytes were distinguished from other erythrocytes based on the fluorescence intensity and the scattered light intensity. The numbers of these two types of cells were counted and the cell ratio between them was calculated. FIG. 13 shows the comparison of the fluorescence of the reticulocytes with that of the total erythrocytes, with the reticulocytes comprising 2.83% of the total erythrocytes. The same anticoagulant-treated blood was detected using the method for the vital staining and microscopic counting of reticulocytes recommended by International Council for Standardization in Haematology (ICSH) and the result indicated that the reticulocytes comprised 2.88% of the total erythrocytes.

Although the present disclosure has been illustrated by way of the above embodiments and particular examples thereof, it will be appreciated by those skilled in the art that various changes, alterations and modifications may be made to the present disclosure without departing from the spirit and scope of the present invention as claimed.

The invention claimed is:

1. A compound having the structure of the following general formula I:

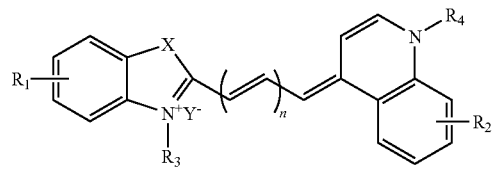

wherein
n is 1, 2 or 3;
X is C(CH$_3$)$_2$, O, S or Se;
R$_1$ and R$_2$ are each independently selected from at least one of the following: H, a halogen, and C$_{1-18}$alkylsulfo, provided that R$_1$ and R$_2$ are not simultaneously H;
R$_3$ and R$_4$ are each independently selected from at least one of the following: C$_{1-18}$alkyl and C$_{1-18}$alkylOR$_5$, provided that R$_3$ and R$_4$ are not simultaneously alkyls when R$_2$ is a halogen;
R$_5$ is a hydrogen atom, acyl or lower alkyl; and
Y$^-$ is an anion.

2. The compound according to claim 1, wherein R$_1$ and R$_2$ are each independently selected from at least one of the following: H, a halogen, and C$_{1-6}$alkylsulfo, provided that R$_1$ and R$_2$ are not simultaneously H.

3. The compound according to claim 1, wherein R$_3$ is C$_{1-6}$alkyl or C$_{1-6}$alkylOR$_5$.

4. The compound according to claim 1, wherein R$_4$ is C$_{1-6}$alkyl or C$_{1-6}$alkylOR$_5$.

5. The compound according to claim 1, wherein R$_5$ is H, C$_{1-3}$alkylCO or C$_{1-6}$alkyl.

6. The compound according to claim 1, wherein X is C(CH$_3$)$_2$, O or S.

7. The compound according to claim 1, wherein n is 1 or 2.

8. The compound according to claim 1, wherein Y$^-$ is a halogen ion, ClO$_4^-$, PF$_6^-$, CF$_3$SO$_3^-$, BF$_4^-$, acetate or p-toluenesulfonate anion.

9. The compound according to claim 1, wherein said compound is selected from:

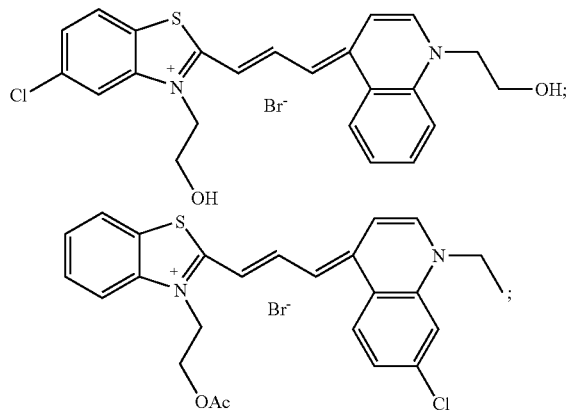

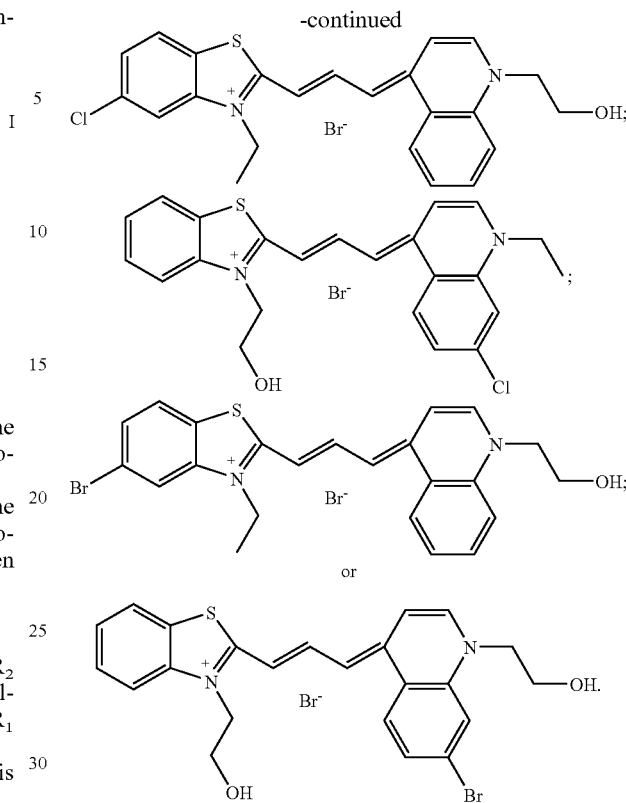

10. A conjugate comprising the compound according to claim 1.

11. A composition for staining biological samples, wherein said composition comprises the compound according to claim 1 or a conjugate thereof.

12. The composition according to claim 11, wherein said biological samples are selected from nucleic acids, erythroblasts or reticulocytes in the blood.

13. A method of staining a biological sample, comprising:
obtaining a compound according to claim 1, or a conjugate thereof, or composition including the compound; and
staining the biological sample with the compound, conjugate or composition.

14. The method according to claim 13, wherein the biological sample is selected from at least one of: nucleic acids, erythroblasts or reticulocytes.

15. A method for analyzing reticulocytes, comprising:
staining a blood sample to be tested with the compound according to claim 1 or a conjugate thereof, or a composition containing the compound according to claim 1 or a conjugate thereof; and
analyzing the stained blood sample in a flow cytometer to detect the reticulocytes.

* * * * *